United States Patent
Gobron et al.

[11] Patent Number: 6,159,220
[45] Date of Patent: Dec. 12, 2000

[54] MEDICAL RETRIEVAL DEVICE

[75] Inventors: Stéphane Gobron, Gosport; Like Que, Bloomington; Tim E. Ward, Bedford; William Curtis White; Tina M. Carpenter, both of Spencer, all of Ind.

[73] Assignee: Scimed Life Systems, Inc., Maple Grove, Minn.

[21] Appl. No.: 09/268,484

[22] Filed: Mar. 11, 1999

[51] Int. Cl.[7] .................................................. A61B 17/22
[52] U.S. Cl. ............................................................ 606/127
[58] Field of Search ................................ 606/1, 106, 113, 606/114, 127; 600/209

[56] References Cited

U.S. PATENT DOCUMENTS

| | | | |
|---|---|---|---|
| 1,054,960 | 3/1913 | Butner | 606/127 X |
| 3,791,387 | 2/1974 | Itoh | 128/320 |
| 4,203,429 | 5/1980 | Vasilevsky et al. | 128/1 R |
| 4,611,594 | 9/1986 | Grayhack et al. | 128/328 |
| 4,633,871 | 1/1987 | Shinozuka | 128/321 |
| 4,691,705 | 9/1987 | Okada | 128/328 |
| 4,807,626 | 2/1989 | McGirr | 128/328 |
| 5,057,114 | 10/1991 | Wittich et al. | 606/127 |
| 5,064,428 | 11/1991 | Cope et al. | 606/127 |
| 5,084,054 | 1/1992 | Bencini et al. | 606/127 X |
| 5,098,441 | 3/1992 | Wechler | 606/113 |
| 5,171,233 | 12/1992 | Amplatz et al. | 606/127 X |
| 5,207,686 | 5/1993 | Dolgin | 606/113 |
| 5,330,482 | 7/1994 | Gibbs et al. | 606/113 |
| 5,421,832 | 6/1995 | Lefebvre | 604/53 |
| 5,496,330 | 3/1996 | Bates et al. | 606/113 X |
| 5,499,981 | 3/1996 | Kordis | 606/41 |
| 5,725,525 | 3/1998 | Kordis | 606/41 |
| 5,895,352 | 4/1999 | Kleiner | 600/209 X |

FOREIGN PATENT DOCUMENTS

98/36694  8/1998  WIPO .

*Primary Examiner*—Jeffrey A. Smith
*Attorney, Agent, or Firm*—Testa, Hurwitz & Thibeault, LLP

[57] ABSTRACT

A medical retrieval device includes a handle, a sheath, and a basket having basket legs and an atraumatic distal tip. The atraumatic tip of the basket is formed, for example, by entwining the ends of the basket legs together at the distal tip of the basket. Baskets with atraumatic tips according to the invention allow the capture of material from difficult to reach areas of the body while reducing the risk of tissue damage.

18 Claims, 19 Drawing Sheets

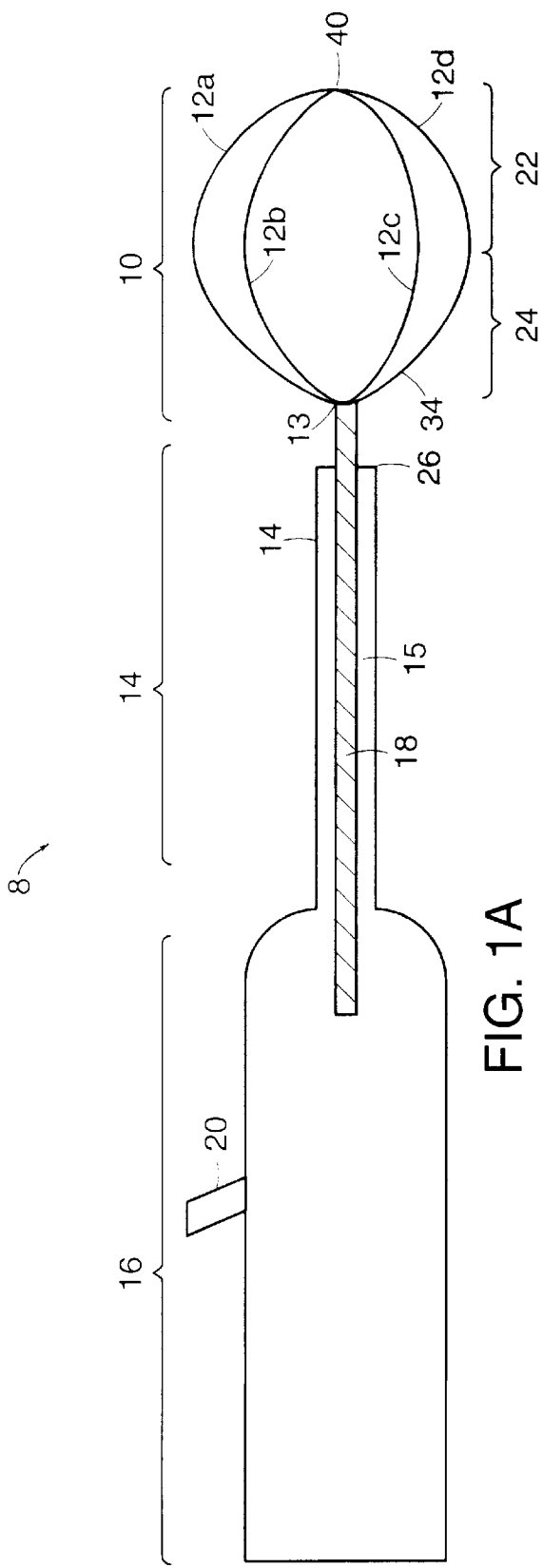
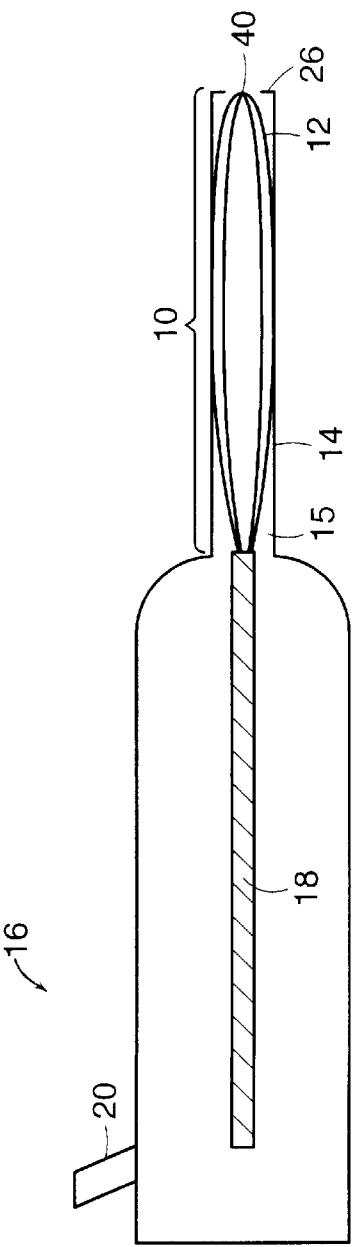
FIG. 1A
FIG. 1B

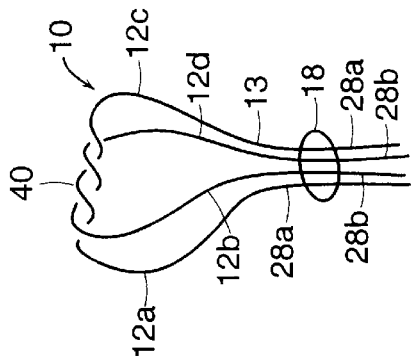
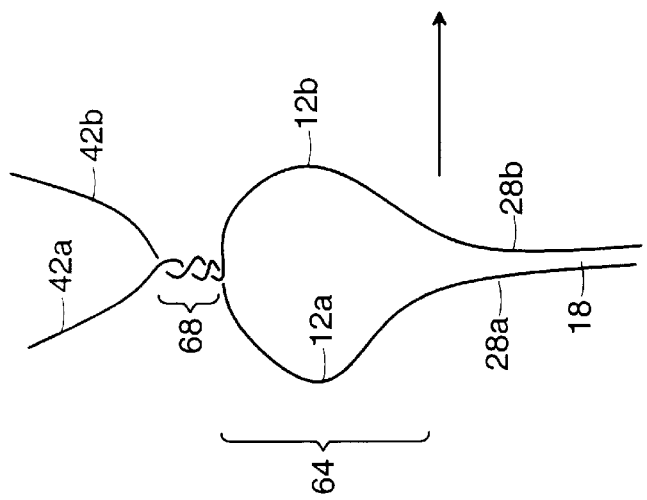
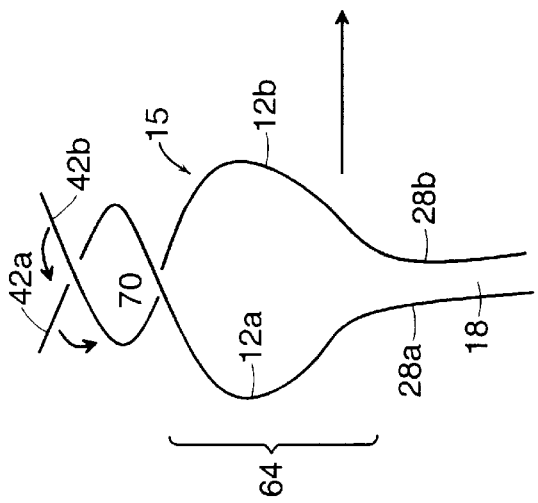
FIG. 4C
FIG. 4B
FIG. 4A

MEDICAL RETRIEVAL DEVICE

TECHNICAL FIELD

The invention relates generally to baskets for retrieving material from within a body. More particularly, the invention relates to medical retrieval baskets that have atraumatic distal ends that are contoured or tipless both to minimize the chances of damage to tissue during use and to enhance the ability of the basket to capture material (e.g., stones) disposed or lodged in "pockets" or other areas that are difficult to access in the body.

BACKGROUND INFORMATION

Known stone retrieval devices typically have baskets that are constructed by joining multiple legs together at a base of the basket and at a distal end or tip of the basket such that a "cage" is formed. At the distal tip, the individual legs are joined by soldering, adhesives, etc. such that a protruding tip results. This protrusion or outward projection at the distal end of the basket can poke tissue and cause tissue trauma. In general, the tips or ends of known baskets protrude outward and thus can cause damage by poking or piercing tissue. Also, the protruding tips of known baskets generally do not permit access to or intimate contact with certain areas within the body such as "pockets," and thus stones residing in such areas are difficult or impossible to retrieve with known baskets.

SUMMARY OF THE INVENTION

It is an object of the invention to provide a retrieval device that does not have a substantially protruding distal basket end or basket tip. That is, a basket according to the invention is substantially atraumatic and does not have any significant distal protrusion or outward projection that can poke tissue, pierce tissue, or otherwise cause trauma to tissue or inhibit or hinder capturing of material.

It is yet another object of the invention to provide a method of using such baskets to retrieve material from within a body. The material can be biological or foreign matter. The material can be, for example, urological stones or any of a variety of any other types of material within a body.

It is another object of the invention to provide a medical device that permits access to and/or intimate contact with certain areas of the body such as pockets where material to be retrieved (e.g. stones) might reside or be lodged, impacted, or embedded. A tipless or contoured basket arrangement can access these areas and retrieve material from those areas whereas a conventional basket with a traumatic tip would not be able to do so because of the protruding tip that prevents intimate contact between the distal end of the basket and body tissue.

A medical device according to the invention is used to treat an internal organ which includes a material such as a calculus or a thromboembolus. The medical retrieval device typically includes an elongated member, a handle, a sheath, and a basket. The elongated member extends within a sheath along an axis from a proximal end to a distal end. The elongated member and the sheath are sized for insertion into a body. The handle is located at the proximal end of the elongated member and the sheath. The basket is positioned at the distal end of the elongated member opposite to the handle. The basket may be withdrawn into or extended from the distal end of the sheath by moving the basket relative to the sheath via an actuating mechanism on or near the handle. Thus, the basket is moveable between a collapsed position, where the basket is enclosed within the sheath, and an extended or opened position, where the basket is extended from and out of the distal end of the sheath.

In one aspect, the invention relates to a medical device comprising a plurality of legs forming a basket. A tip, at a distal end of the basket, comprises two or more legs entwined together. A basket tip, according to the invention, is atraumatic, i.e., substantially devoid of points or protrusions that might otherwise poke or cause injury to tissue.

Embodiments of this aspect of the invention can include the following features. For example, the basket of the device can have three or more legs. Also, the legs of the basket can be formed from a single wire or a plurality of wires. The device can have an elongated member extending from a proximal end of the basket. The elongated member and the basket legs can be formed from a single (common) wire. The tip of the basket can be formed by entwining the basket legs. Entwining the legs can be accomplished in similar ways such as by braiding or twisting the legs together. Alternatively, the legs can be coupled together at the tip by knotting, looping or weaving. A portion of a basket tip, according to the invention, is atraumatic, i.e., devoid of points or protrusions that might otherwise poke or cause injury to tissue, and it enhances the ability of the basket to capture material located in difficult to access areas of the body.

In another aspect, the invention relates to a medical device comprising a distal end portion and a plurality of legs extending proximally from the distal end portion. The distal end portion and the plurality of legs are formed integrally from a single twisted wire.

Embodiments of this aspect of the invention can include the following features. For example, at least a portion of one of the legs can be braided. The legs can be formed from at least one twisted wire. The plurality of legs can be twisted together at the distal basket end portion to form an atraumatic basket. At least one of the legs can be braided.

In yet another aspect, the invention relates to a medical device comprising a distal end portion and a plurality of pairs of basket legs extending proximally from the distal end portion. Each of the pairs of baskets legs can be formed from a single twisted wire. The distal end portion can be formed by coupling together the pairs of basket legs.

Embodiments of this aspect of the invention can include the following features. For example, the legs can be formed of metal, or polymers, or any other suitable material such as a composite material. The legs can be joined at a basket base to other legs and/or affixed to an elongated member. The legs can be joined at the base by crimping, twisting, soldering, gluing, welding, or by other means known to one skilled in the art.

Methods of making and using such devices are also part of the invention. One method of making a device is to introduce a plurality of crimps along the length of a wire. The wire is then subjected to tension and twisted to cause a length of the wire to twist on itself thereby forming a braided leg. A number of legs can be made from the single length of wire. One or more wires can be inserted between the twists of a braided leg to form additional legs of the basket. The inserted wire can be twisted, as described above, to form one or more additional braided legs.

One method of retrieving material from a body using such devices includes inserting the device into a body and capturing the material with the device. The device is then withdrawn from the body to remove the captured material from the body.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

FIG. 1A shows an embodiment of a medical retrieval device according to the invention with a basket in a fully-extended or open position.

FIG. 1B shows the device of FIG. 1A with the basket in a collapsed or retracted position.

FIGS. 4A–4C show certain stages in the construction of a basket formed from two wires.

FIG. 5F shows an embodiment of a single wire basket having a knotted atraumatic tip.

DESCRIPTION

Figure 2A:
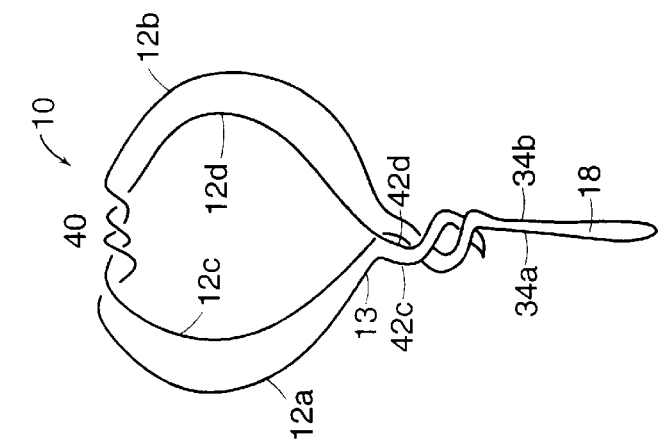
FIGS. 2A–2C show certain stages in the construction of a single wire basket structure.

All of the following embodiments of the invention have at least one thing in common, a substantially atraumatic basket tip according to the invention. Referring to FIG. 1A, one embodiment of a retrieval device 8 for removing material from a body includes a handle portion 16, a sheath portion 14, and a basket 10. The handle 16, the sheath 14, and the basket 10 are not shown in their correct size or proportion to each other. The sheath 14 typically is much longer than the handle 16 or the basket 10 to allow insertion into a body cavity, canal, or tract. The basket 10 can be made of resilient material, such as metal wires, forming three or more basket legs 12a, 12b, 12c, 12d.

With continued reference to FIG. 1A, the basket 10 is the type that can be collapsed within the sheath 14 for entry into the body. The sheath 14 has at least one lumen 15 therein, and it extends from the handle to a distal sheath end 26. An elongated member 18 such as a cable, coil, shaft, guidewire, or mandril wire 18 extends within the lumen 15 from an actuating mechanism 20 in the handle portion 16 to a base 13 of the basket where the elongated member 18 is joined to the basket base 13. Operation of the actuating mechanism 20 by an operator causes the basket 10 to move relative to the sheath 14 between a collapsed position within the sheath 14 as illustrated in FIG. 1B, to an extended position outside of the sheath 14 where the basket 10 is open/extended and extending beyond the distal end of the sheath 26 as shown in FIG. 1A. With the basket withdrawn into and collapsed within the sheath 14 as shown in FIG. 1B, the basket 10 can be inserted into the body by an operator to a site in the body where the material to be retrieved is located (e.g., a stone in the ureter). The basket 10 is then moved relative to the sheath 14 and placed in the extended position illustrated in FIG. 1A, such that the basket 10 dilates the body tract and can be manipulated by the operator to entrap or capture material within the basket 10. The basket 10 can then be moved relative to the sheath 14 to cause the legs 12a, 12b, 12c, 12d of the basket to close around the material and capture it. The captured material is then withdrawn from the body along with the sheath and the basket that is holding the material.

With continued reference to FIG. 1A, the basket 10 has a proximal end portion 24, a distal end portion 22, and a tip 40. The tip 40, in accordance with the invention, is devoid of protrusions, fasteners, or outward projections. There is no adhesive used at the basket tip 40 to hold the basket legs 12a, 12b, 12c, 12d together as at least the basket tip 40 is formed by entwining or coupling the legs 12a, 12b, 12c, 12d of the basket 10 together at the distal tip 40. Entwining or coupling of the basket legs 12a, 12b, 12c, 12d at the basket tip 40 can be accomplished by twisting, spiraling, wrapping, or braiding together two or more legs of the basket 10. Coupling could also be accomplished alternatively by looping, knotting, or weaving the legs together. The distal end portion 22 of a basket 10, thereby, is substantially atraumatic in that the basket tip 40 is devoid of outward projections or protrusions that might cause injury or trauma to tissue and/or that presents an impediment to contacting the tip 40 of the basket 10 directly and intimately with tissue.

Figure 2B:
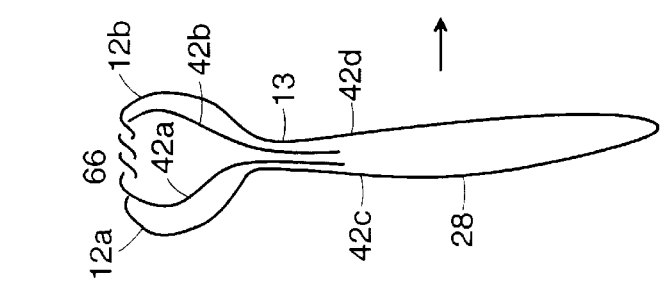
Figure 2C:
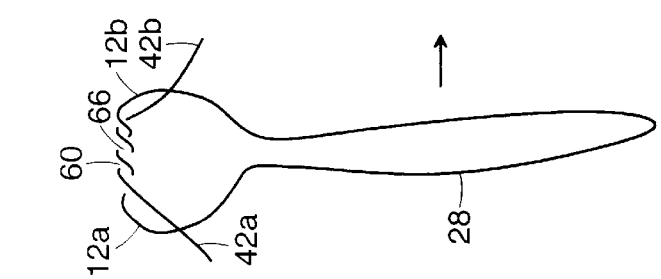
Figure 2D:
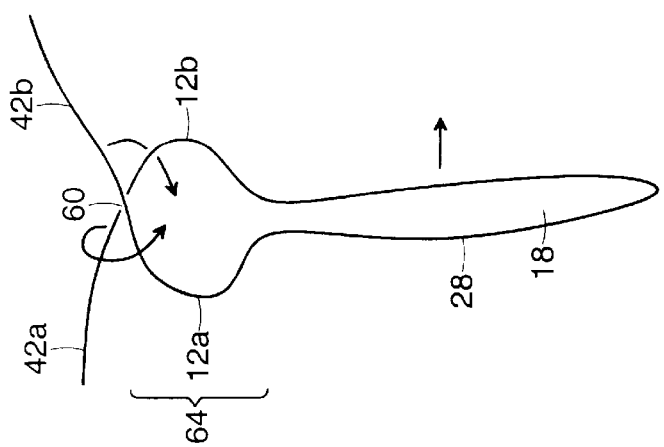
FIG. 2D shows an embodiment of a basket of the invention made according to the method illustrated in FIGS. 2A–2C.
Figure 2E:
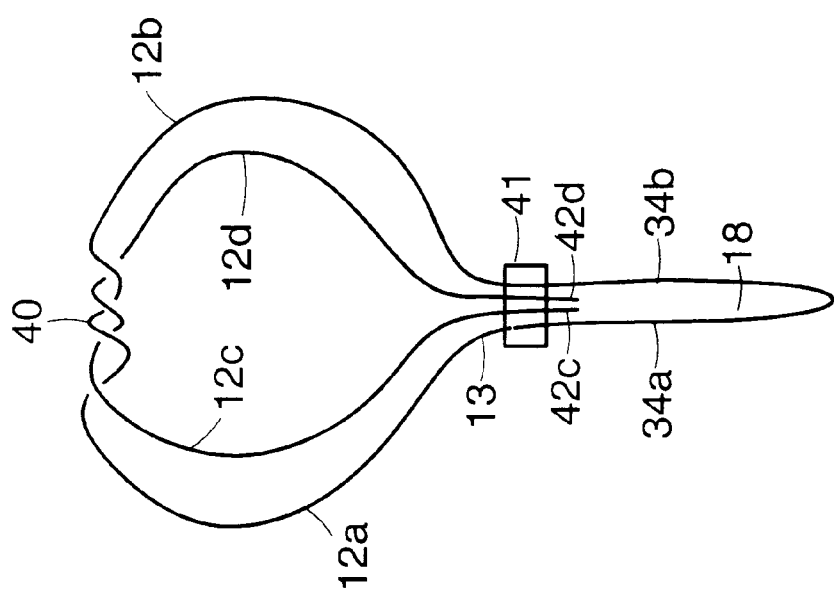
FIG. 2E shows another embodiment of a basket of the invention made according to the method illustrated in FIGS. 2A–2C.

In one embodiment, a medical device of the invention comprises a plurality of legs 12 that form a medical retrieval basket. The device also includes an atraumatic basket tip 40. In FIGS. 2A–2C, a series of steps or stages, herein referred to as the horizontal method, are illustrated to construct a basket 10 having four legs 12a, 12b, 12c, 12d and an atraumatic tip 40, and an elongated member 18, all made from a single wire 28. Referring to FIG. 2A, in a first step, a single wire 28 is shaped to form an elongated member 18, a basket region 64 comprised of legs 12a and 12b, and two end segments 42a, 42b of the legs 12a, 12b formed by the wire 28. The intersection of the end segments 42a and 42b is the nascent site of an atraumatic basket tip 40 illustrated in FIGS. 2D–2E. In a subsequent step illustrated in FIG. 2B, end segments 42a and 42b are entwined by twisting or wrapping end segments 42a and 42b in the direction indicated by the arrows around basket legs 12a, 12b at a distal end 60 of the basket region 64. With continued reference to FIG. 2B, in particular, end segment 42a is twisted around basket leg 12a and end segment 42b is twisted around basket leg 12b to form a twisted segment 66. Referring to FIG. 2C, end segment 42a and 42b can become additional legs 12c, 12d of the basket 10 by drawing the untwisted portions of end segments 42a, 42b proximally, i.e., toward a basket base 13. Heat treatment, cold-forming, or other shaping processes using a ball-shaped die is then performed to shape the legs into a basket shape. Twisted segment 66 in FIG. 2C forms the atraumatic basket tip 40 in FIG. 2D. With continued reference to FIG. 2D, the free ends 42c, 42d of end segments 42a, 42b may be joined to elongated member 18 by twisting free ends 42c, 42d on elongated member 18 to complete construction of a three-dimensional basket 10 with an atraumatic tip 40. Other means 41 of joining the free ends 42c, 42d to the elongated member 18, such as by crimping, gluing, welding, or soldering, could also be used as shown in FIG. 2E. Baskets with a different number of legs may also be constructed according to the invention. A three leg basket, for example, can be formed by trimming away one of the end segments, 42a or 42b, adjacent to tip 40 and drawing the remaining end segment proximally toward the basket base 13 to form a three leg basket (not shown). In other embodiments, the basket has a different number of legs than the four legs shown, e.g., five or six legs.

Figure 3A:
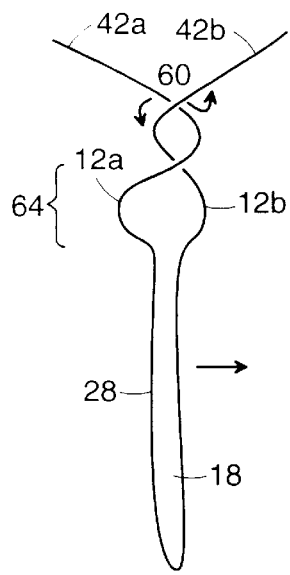
FIGS. 3A–3D show another series of stages in the construction of a single wire basket structure.
Figure 3B:
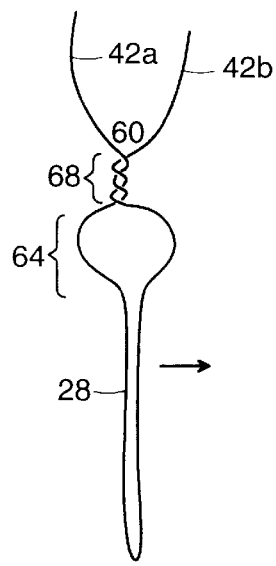
Figure 3C:
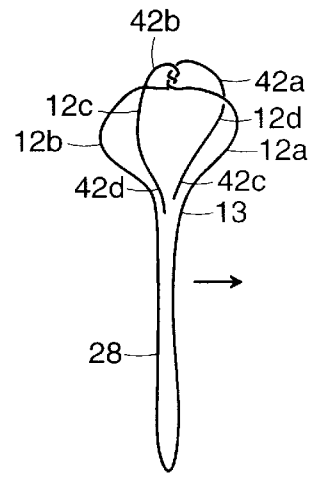
Figure 3D:
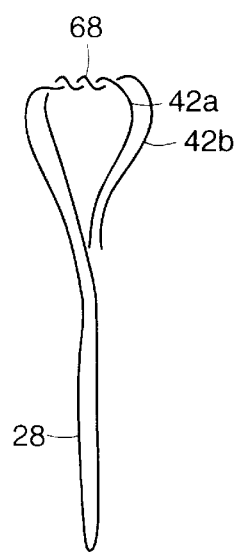
Figure 3E:
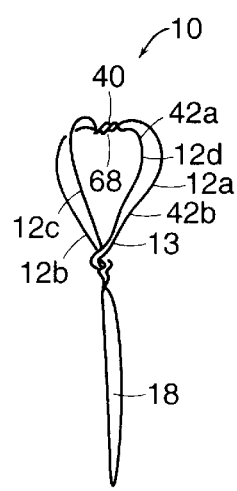
FIG. 3E shows an embodiment of a basket of the invention made according to the method illustrated in FIGS. 3A–3D.
Figure 3F:
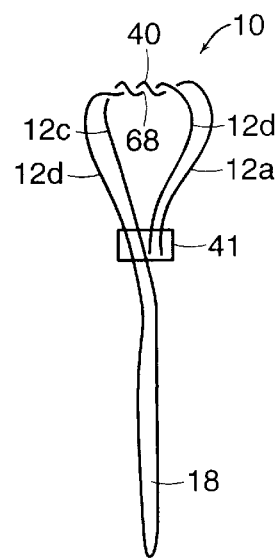
FIG. 3F shows another embodiment of a basket of the invention made according to the method illustrated in FIGS. 3A–3D.

In FIGS. 3A–3D, a series of steps or stages are shown to illustrate another method of manufacturing a four leg basket 10 with atraumatic tip 40 and elongated member 18 all from a single wire 28, hereinafter referred to as the vertical method. Referring now to FIG. 3A, in a first step, a single wire 28 is shaped to form an elongated member 18, a basket region 64 comprising legs 12a and 12b, and two end segments 42a and 42b of the legs 12a, 12b formed by the wire 28. End segments 42a and 42b intersect at the distal end 60 of the basket region 64. In a subsequent step, end segments 42a and 42b are entwined by twisting together end segment 42a and 42b at distal end 60 in the direction of the arrows shown in FIG. 3A. FIG. 3B illustrates a twisted segment 68 comprising vertical twists of end segments 42a and 42b at the distal end 60 of the basket region 64. Referring now to FIG. 3C, end segments 42a and 42b are drawn proximally to form the third and fourth basket legs, 12c and 12d, respectively, of the basket 10. Alternatively, referring now to FIG. 3D, twisted segment 68 is moved proximally with end segments 42a and 42b to form legs 12c and 12d. Heat treatment, cold-forming, or other processes using a ball-shaped die is then performed to shape the legs into a basket shape. The free ends 42c, 42d of end segments 42a, 42b may be joined to elongated member 18 by twisting, as shown in FIG. 3E, or by any other means 41 known in the art, such as by crimping, gluing, welding, or soldering, as shown in FIG. 3F. Referring now to FIG. 3E or FIG. 3F, a basket 10 includes an atraumatic basket tip 40 comprising a twisted segment 68 and four basket legs 12a, 12b, 12c, and 12d. Baskets with a different number of legs such as three, five, or six legs are also contemplated by the invention.

In FIGS. 4A–4B, a series of steps are illustrated for constructing a basket having four legs 12a, 12b, 12c, 12d and an atraumatic tip 40, and an elongated member 18 comprised of two wires 28a, 28b. Referring to FIG. 4A, each of two wires, 28a and 28b are combined to form the structure 15 illustrated in FIG. 4A, the structure having an elongated member 18, a basket region 64, an end segment 42a of leg 12a formed by wire 28a, and an end segment 42b of leg 12b formed by wire 28b. Following steps similar to the steps illustrated in FIGS. 3A–3D, referring now to FIGS. 4A–4B, end segments 42a and 42b are twisted together at approximately a midpoint 70 of wire 28a and 28b to form a twisted segment 68. By applying heat treatment, cold-forming, or other known processes using a ball-shaped die, four legs, 12a, 12b, 12c, 12d, shown in FIG. 4C are thereby formed from a portion of the two wires 28a and 28b on each side of the twisted segment 68. An atraumatic tip 40, as illustrated in FIG. 4C, is formed from twisted segment 68. The four legs 12a, 12b, 12c, 12d are secured to one another or to an elongated member 18 at the basket base 13 to complete construction of the basket 10 comprising four legs 12a, 12b, 12c, 12d and an atraumatic tip 40 formed from two wires 28a, 28b.

Figure 5A:
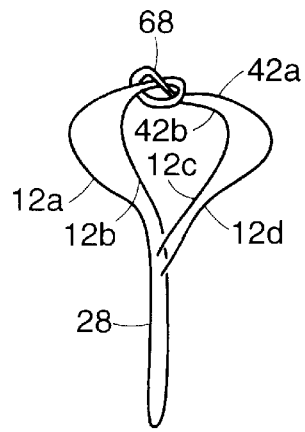
FIG. 5A shows an embodiment of a single wire basket having a knotted atraumatic tip.
Figure 5B:
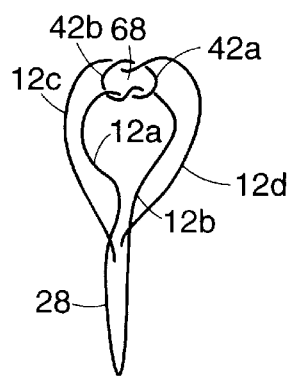
FIG. 5B shows another embodiment of a single wire basket having a knotted atraumatic tip.
Figure 5C:
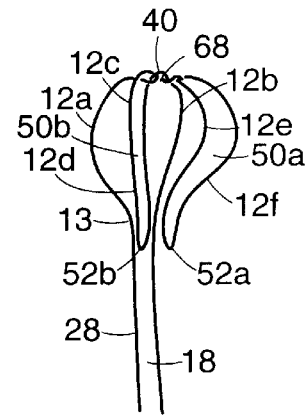
FIG. 5C shows another embodiment of a single wire basket having twisted loops at the atraumatic tip.
Figure 5D:
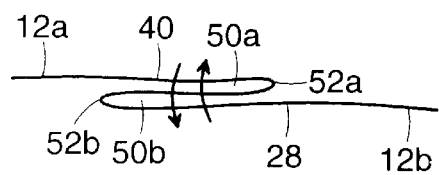
FIG. 5D shows a method for constructing the atraumatic tip illustrated in FIG. 5C.
Figure 5F:
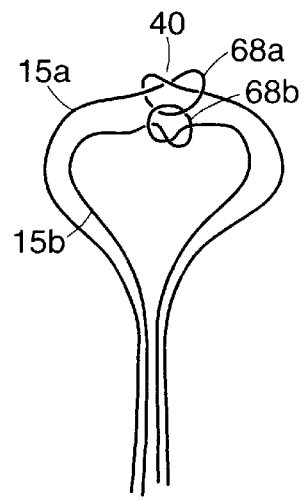
FIGS. 5E and 5F show another embodiment of a two-wire basket having a knotted atraumatic tip.
Figure 5E:
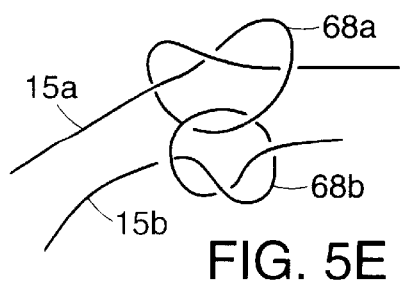

Other methods for entwining the basket legs at the distal end of a basket to form an atraumatic tip are illustrated in FIGS. 5A–5E. Referring to FIG. 5A, a four leg, single wire basket 10 of the invention is illustrated. The steps used to construct the basket in FIGS. 5A and 5B are similar to the steps illustrated in FIGS. 2A–2C and 3A–3D. The difference between the baskets illustrated in FIGS. 5A–5B and 5E and the baskets in FIGS. 2A and 3A, is that the step that forms atraumatic tip 40 in FIGS. 5A–5B and 5E is accomplished by making a knot 68, such as an overhand knot (FIG. 5A), a granny knot (FIG. 5B), or a square knot in end segments 42a, 42b, rather than by twisting as pertains to FIGS. 2A and 3A.

In another embodiment of the invention, with reference to FIG. 5C, a basket having 6 legs and an atraumatic tip 40, and an elongated member 18 is constructed from a single wire. As illustrated in FIG. 5D, to construct the basket illustrated in FIG. 5C, two loops 50a and 50b, are made along the length of a wire 28. The two loops 50a, 50b are coupled together by twisting the two loops 50a, 50b together at approximately a midpoint along the wire 28, in the direction of the arrows shown in FIG. 5D, to form a twisted segment 68. The twisted segment 68 forms an atraumatic tip 40 as illustrated in FIG. 5C. The ends 52a, 52b of the loops are drawn proximally toward basket base 13 to form four additional legs 12c, 12d, 12e, 12f of a three-dimensional basket with an atraumatic tip 40. In other embodiments, the basket is formed from a different number of loops than the two loops illustrated (e.g., three, four, five or more) and has a different number of legs than the six legs shown (e.g., 8, 10 or more legs). Additionally, the basket may be formed from a plurality of wires, each wire forming at least one loop.

In another embodiment, a series of steps are required for manufacturing a medical retrieval device including an atraumatic basket, illustrated in FIG. 5F, formed from at least two wires, each wire having a knot, the knots of each wire knotted together at the distal basket end. The steps begin by cutting at least a first and a second piece of, for example, Nitinol wire 15a, 15b to 300 cm in length. The second wire is placed over and perpendicular to the first wire. Next, a first single overhand knot 68a is placed in the first wire 15a securing the second wire 15b within the knot 68a of the first wire 15a. The first overhand knot 68a is tightened. A second single overhand knot 68b is tied into the second wire 15b securing the wire(s) of the knot from the first wire 15a within the knot 68b of the second wire. The knot 68b of the second wire is tightened. These steps may be repeated with additional wires for a basket having more than four legs. The knotted wires 15a, 15b are picked up and with two wires in each hand, the knots 68a, 68b are pulled tighter. The knotted end 40 of the basket is illustrated in FIG. 5E as a greatly expanded view of the basket end 40 in FIG. 5F.

After the knots 68a, 68b have been tightened, the knots are glued to the center of a basket forming ball with, for example, 4014 Loctite adhesive. The forming ball is placed in a table vise with the basket tip end down.

Next, a cannula (not shown) is slid over the wire ends to the basket forming fixture and the knot is aligned with the tip pin on the bottom of the ball fixture. One drop of adhesive is placed on the cannula and held until dry.

A long mandril (not shown) is slid over the four wires and the cannula and an adhesive, for example, Loctite 498 is applied to hold the wires straight during the heat treating step. The entire forming fixture is wrapped in 3–4 layers of aluminum foil. The foil covered fixture is dipped in molten solder and secured with a holding fixture. The fixture is removed from the molten solder after the appropriate time and submerged in cooling water. The forming fixture is disassembled and the wires are carefully removed and wiped with alcohol to remove any residue.

The joints on each device are soldered. The wires are cleaned and MEDI-GLIDE II is applied. The proper length catheter and handle assembly is assembled on the wire assembly.

Figure 6A:
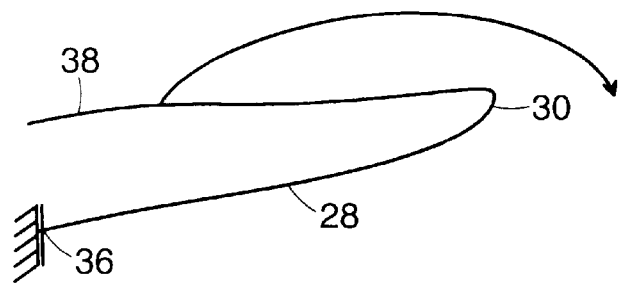
FIGS. 6A–6D show certain stages in the construction of a single wire braided leg.
Figure 6B:
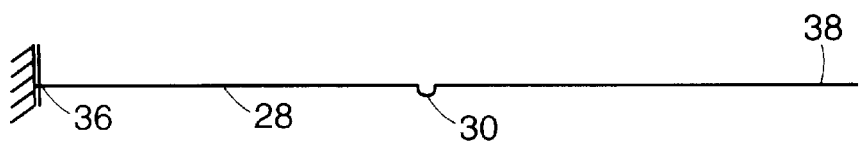
Figure 6C:
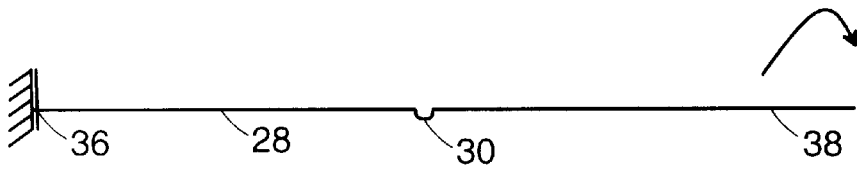
Figure 6D:
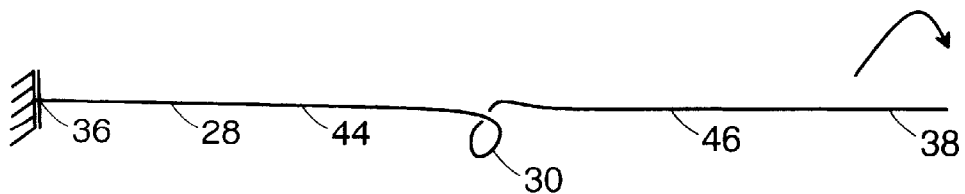
Figure 6F:
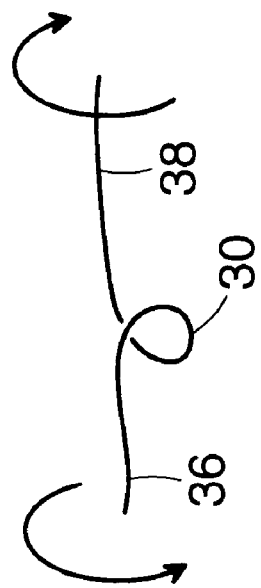
FIG. 6F shows an alternate method for twisting wire from that shown in FIG. 6D.
Figure 6E:
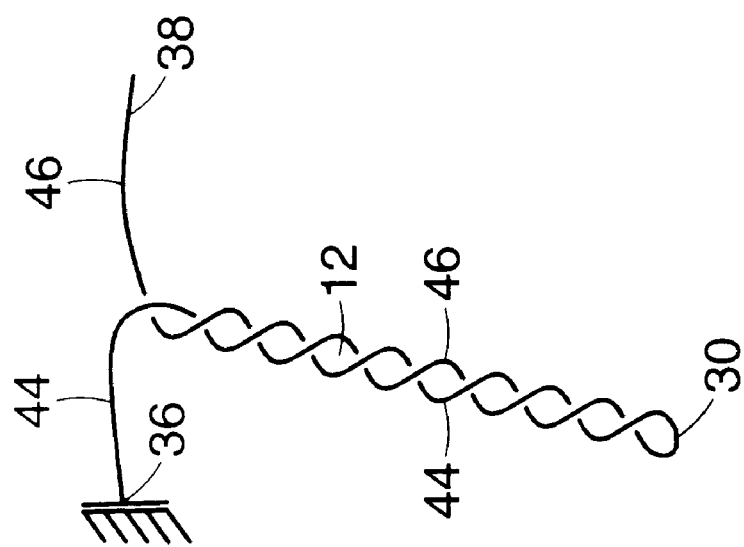
FIG. 6E shows an embodiment of a braided leg made according to the method illustrated in FIGS. 6A–6D.

In another aspect, the invention relates to a medical device comprising a distal end portion and a plurality of legs extending proximally from the distal end portion. The distal end portion and the legs are formed from a single twisted wire. One or more of the basket legs can be braided. Referring to FIGS. 6A–6E, an exemplary series of steps or stages in the construction of a braided leg 12 from a single wire 28 is illustrated. Referring to FIG. 6A, in a first step, a braided leg 12 is formed by introducing a crimp, ridge or fold 30 along a length of wire 28. A crimp 30 can be made by, first, bending the wire 28 at a point along its length, and then straightening the wire 28 as indicated by the arrow in FIG. 6A. Referring to FIG. 6B, the wire 28 is straightened only to the extent that a crimp, ridge, or fold 30 remains at the site along the length of wire 28 where the wire 28 was bent. Referring to FIG. 6C, in a subsequent step, one end 36 of the length of wire 28 is attached to a support. The length of wire 28 is twisted, as illustrated by the arrow, from the opposite, free end 38 while the wire 28 is under tension. Referring to FIG. 6D, as the wire 28 is twisted, a first segment or strand 44 of wire 28 on one side of the crimp 30 begins to coil on a second segment or strand 46 of wire 28 on the other side of the crimp 30 as tension on wire 28 is gradually released. A braided leg 12 is formed, thereby, comprising a first strand 44 and a second strand 46 as illustrated in FIG. 6E. The crimp 30 forms one end of the braided leg 12.

Alternatively, to form a braided leg, neither end of wire 28 is attached to a support and both ends of wire 28 are free ends (not shown). The free ends of wire 28 are twisted in opposite directions as illustrated by the arrows in FIG. 6F, to form a braided leg.

Figure 7A:
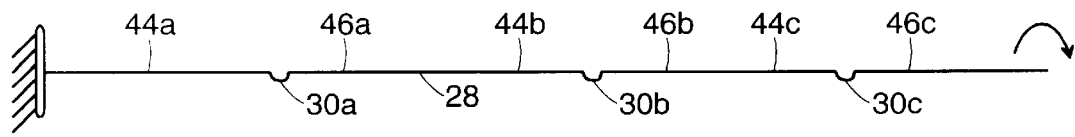
FIGS. 7A–7D show certain stages in the construction of a single wire distal end portion of a basket with a plurality of braided legs.
Figure 7B:
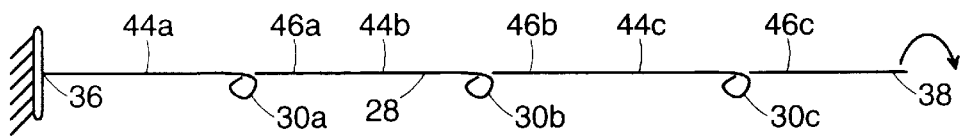
Figure 7C:
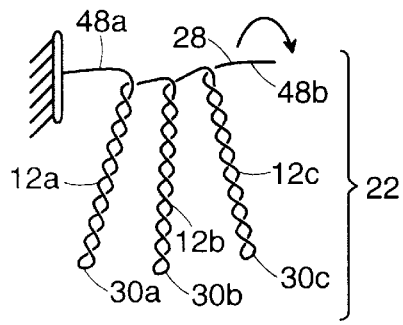
Figure 7D:
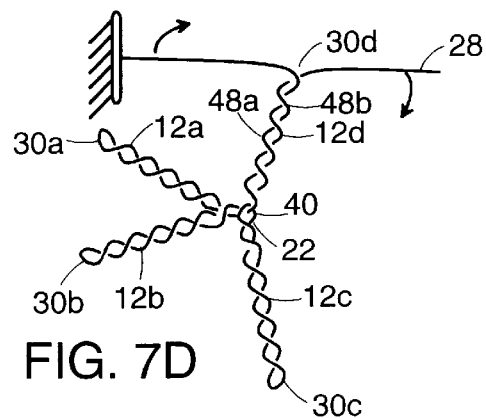

In another embodiment, as shown in FIG. 7D, a single wire, distal end portion of a basket structure according to the invention can have four braided legs. Referring to FIG. 7A, the steps in making a distal end portion 22 of a basket structure having four legs 12a, 12b, 12c, 12d begin by introducing three crimps 30a, 30b, 30c in a length of wire 28 by the method for making a crimp illustrated above in FIGS. 6A and 6B. Each of the crimps 30a, 30b, and 30c are made by first bending, followed by straightening the wire 28 in the manner described above and illustrated by FIGS. 6A–6C. Referring to FIG. 7B, one end 36 of the length of wire 28 is fixed to a support while the length of wire 28 is twisted, as shown by the arrow, at the opposite or free end 38 with wire 28 under tension. Still referring to FIG. 7B, as the wire 28 is twisted, the segment or strand 44a of wire 28 on one side of crimp 30a coils on a segment or strand 46a of wire 28 on the other side of crimp 30a. Segment or strand 44b of wire 28 on one side of a crimp 30b coils on a segment or strand of wire 46b on the other side of crimp 30b, and so on along the length of wire on each side of a crimp. With reference to FIG. 7C, from three crimps 30a, 30b and 30c, three braided legs 12a, 12b, and 12c are formed. One end of each of the braided legs 12a, 12b, and 12c is formed by crimp 30a, 30b, and 30c, respectively. With reference to FIG. 7D, after three braided legs are formed in the manner described above and illustrated in FIGS. 7A–7C, the remaining uncoiled segments 48a and 48b of wire 28 are twisted or coiled together in the direction of the arrows shown in FIG. 7D to form a fourth braided leg 12d of a distal end portion 22 of a basket. Distal end portions of a basket having other than the four braided leg structure 22 illustrated in FIG. 7D, such as 3, 5, 6, 7 or more legs, are also contemplated by the invention. For example, a three braided leg distal end portion according to the invention may be formed from a single wire by following the steps for twisting a wire with two crimps in the manner described above.

Figure 7E:
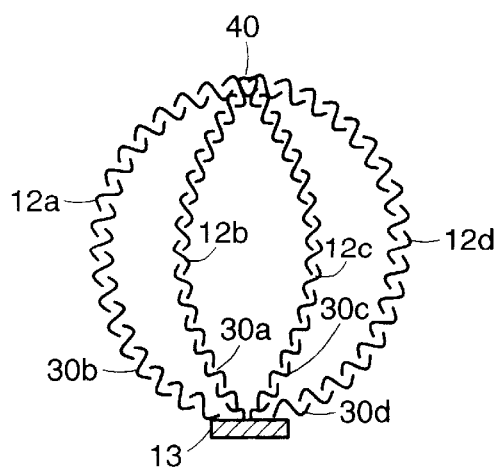
FIG. 7E shows an embodiment of a basket made from the structure illustrated in FIG. 7D.

With reference to FIG. 7E, a basket 10 having four braided legs 12a, 12b, 12c, 12d formed from a single wire 28 is illustrated. The basket structure illustrated in FIG. 7E is constructed by following the steps for making a distal end portion 22 with four braided legs 12a, 12b, 12c, 12d in the manner described above and illustrated in FIGS. 7A–7D. The ends 30a, 30b, 30c, 30d of the braided legs 12a, 12b, 12c, 12d of the distal end portion 22 in FIG. 7D are drawn together at basket base 13 and secured to one another, as shown in FIG. 7E, or to an elongated member (not shown), to form a basket formed from a single wire having four braided legs.

Figure 8:
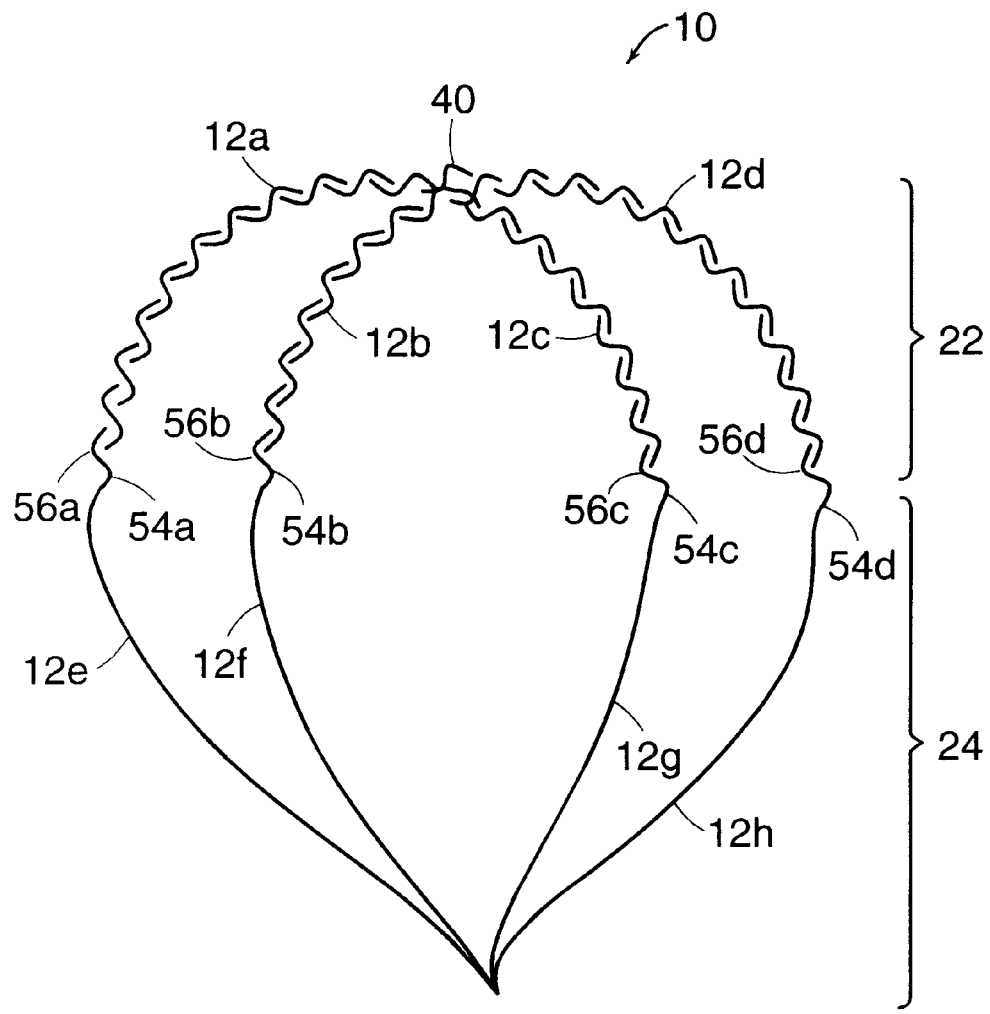
FIG. 8 shows an embodiment of a basket having a distal end portion different from a proximal end portion of the basket.

In another embodiment, the basket, according to the invention, may have a distal basket portion comprising braided legs and a proximal basket portion comprising non-braided legs. Referring to FIG. 8, a basket has a distal end portion 22 and a proximal end portion 24. A distal end portion 22 of a basket 10, similar to the distal end portion illustrated in FIG. 7D, comprises four braided legs 12a, 12b, 12c, 12d. A proximal portion 24 of the basket comprises four non-braided legs 12e, 12f, 12g, 12h. Proximal ends 56a, 56b, 56c, 56d of the four legs of the distal end portion 22 of the basket 10 are joined to a corresponding distal end 54a, 54b, 54c, 54d of the four non-braided legs 12e, 12f, 12g, 12h of the proximal portion 24 of the basket 10. The legs of the proximal portions 12e, 12f, 12g, 12h and the legs of the distal end portions 12a, 12b, 12c, 12d of the basket 10 may be secured to one another by twisting together their ends, or by gluing, welding, soldering, or by any other means known to one skilled in the art. The relative contribution of the distal end portion 22 to the overall size of the basket 10 may be greater or lesser than that represented in FIG. 8. The proximal end portion 24 of the basket 10 may include exclusively braided legs or exclusively non-braided legs or a combination of braided and non-braided legs. Thus, according to the invention, a basket 10 may have a distal end portion 22 having a plurality of braided legs and a proximal end portion 24 having braided or non-braided legs or a combination of braided and non-braided legs.

Figure 9A:
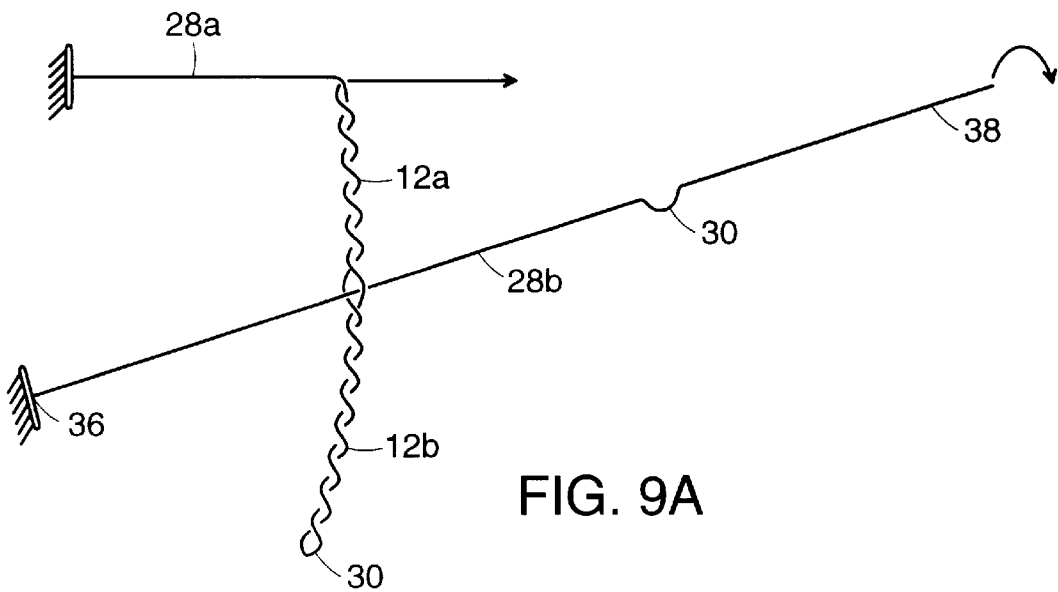
FIGS. 9A–9B show the stages in construction of a two-wire, four-leg atraumatic tip of a medical retrieval basket.
Figure 9B:
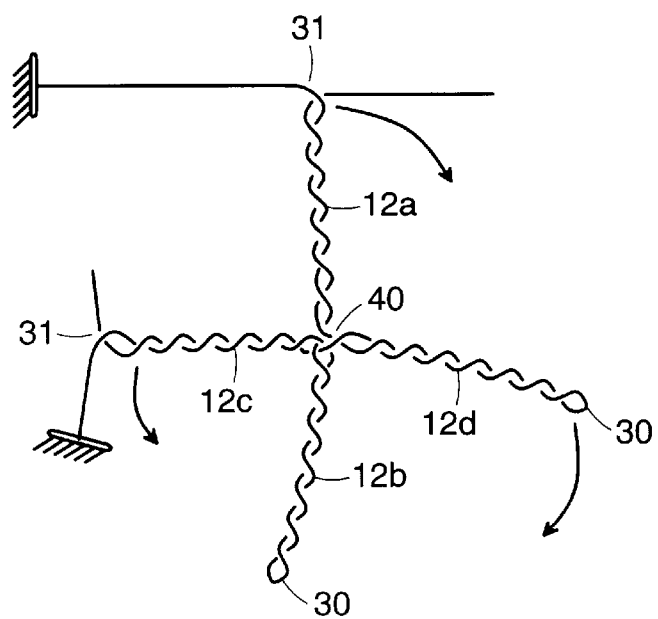
Figure 9C:
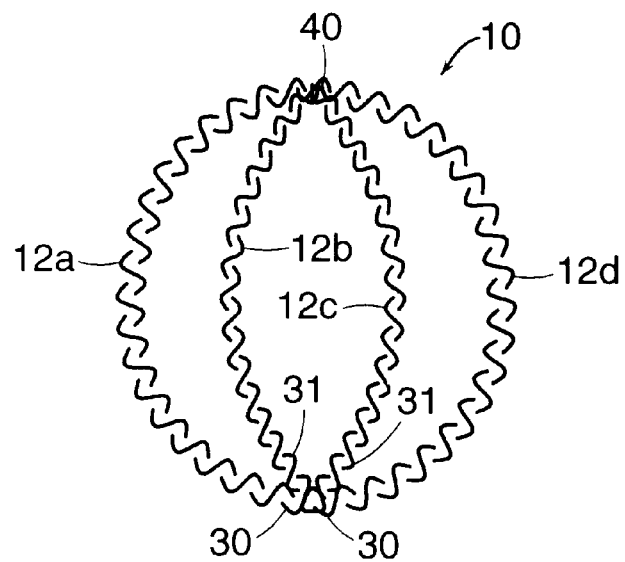
FIG. 9C shows an embodiment of a four leg basket made according to the stages illustrated in FIGS. 9A–9B.

In another embodiment of the invention, a basket includes a plurality of pairs of braided legs, each pair of legs being constructed from a single wire. With reference to FIGS. 9A–9D, a series of steps for constructing a four leg embodiment of a basket 10 comprising two pairs of single wire braided legs is illustrated. With reference to FIG. 9A, a single wire 28b having a crimp 30 introduced along the length of the wire 28b in the manner illustrated in FIGS. 6A–6B, is inserted between the braids of a braided leg 28a. Braided leg 28a is constructed according to the steps illustrated in FIGS. 6C–6E. By inserting the crimped wire 28b between the braids of braided wire 28a, the braided wire 28a is "divided" into two legs, i.e., a pair of legs 12a and 12b. A second pair of braided legs 12c and 12d, shown in FIG. 9B, is formed by twisting wire 28b at the free end 38 while the wire is under tension. A first pair of braided legs 12a, 12b, and a second pair of braided legs 12c, 12d, are thereby entwined or coupled together at the intersection of the two pairs of legs as illustrated in FIG. 9B. The closed ends 30 and the opposite ends 31 of each of the pairs of legs are drawn proximally, as shown by the arrows in FIG. 9B, to form a three-dimensional basket 10 of the invention having two pairs of braided legs 12a, 12b, 12c, 12d as shown in FIG. 9C.

Figure 9D:
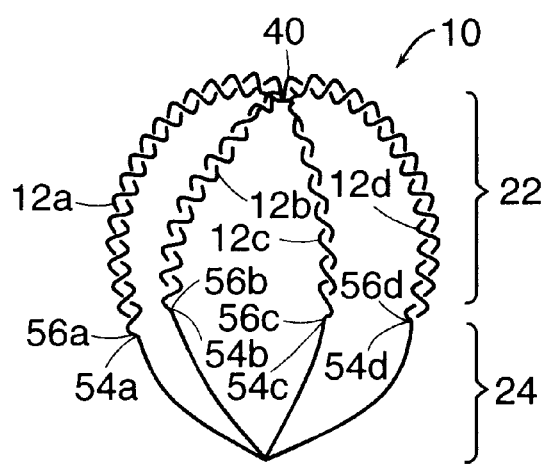
FIG. 9D shows another embodiment of a four leg basket made according to the method illustrated in FIGS. 9A–9B.

In another embodiment, the structure represented in FIG. 9B, constructed from two wires, may form a distal end portion 22 of a basket, similar to the basket shown in FIG. 8, comprised of pairs of braided legs. Referring now to FIG. 9D, a basket 10 having four legs 12a, 12b, 12c, 12d and a braided distal portion 22 and a non-braided proximal portion 24 may be constructed by applying the structure represented in FIG. 9B as a distal end portion 22 of a basket 10. The proximal ends 56a, 56b, 56c, and 56d of the legs 12a, 12b, 12c, 12d of the distal end portion 22 are attached to the corresponding distal ends 54a, 54b, 54c, and 54d of the legs 12a, 12b, 12c, 12d of the proximal portion 24 to form a basket 10 comprising braided and non-braided portions.

Referring still to FIG. 9D, in other embodiments, the basket 10 may have a different number of legs than that shown (e.g., 6, 8, or more legs) and may include more than two pairs of braided legs.

Figure 9E:
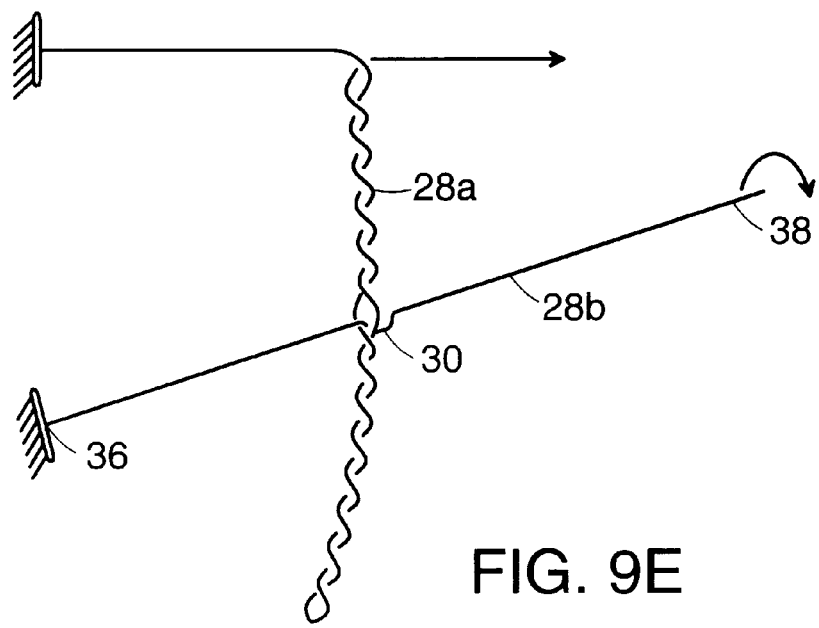
FIGS. 9E–9F show the stages in construction of a two-wire, three-leg basket.
Figure 9F:
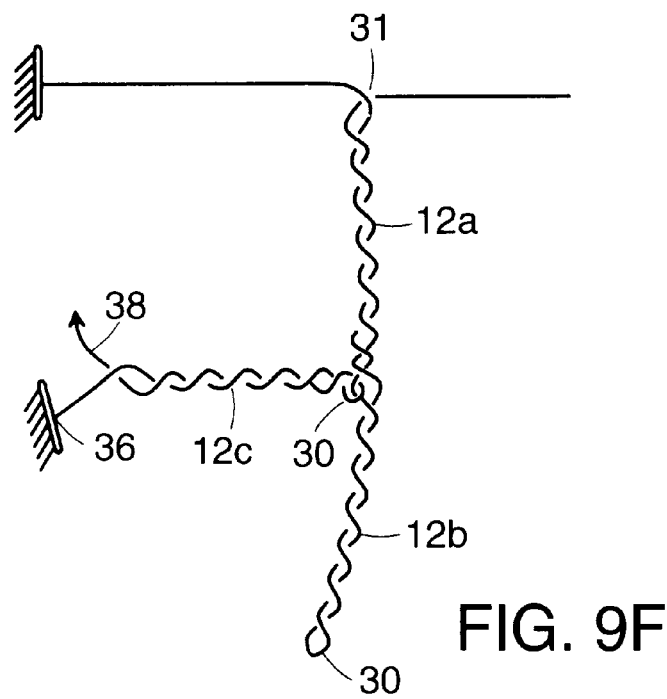

Another embodiment of the invention may include a two wire, three leg basket having a pair of braided legs entwined with a single braided leg. A basket having these features may be constructed by inserting wire 28b, shown in FIG. 9E, between the braids of wire 28a until crimp 30 of wire 28b intersects wire 28a. Wire 28b is twisted in the manner illustrated in FIG. 9A to form a third (but not a fourth) braided leg 12c on one side of wire 28a. Thus, three braided legs 12a, 12b, 12c, formed from a pair of braided legs entwined with a single braided leg is illustrated in FIG. 9F.

Figure 9H:
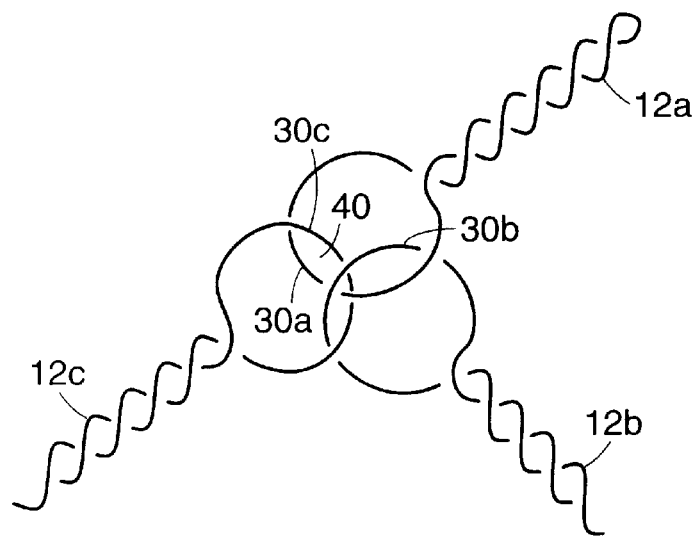
FIGS. 9G–9H show the stages in construction of an atraumatic distal basket tip having linked ends of three-braided legs.
Figure 9G:
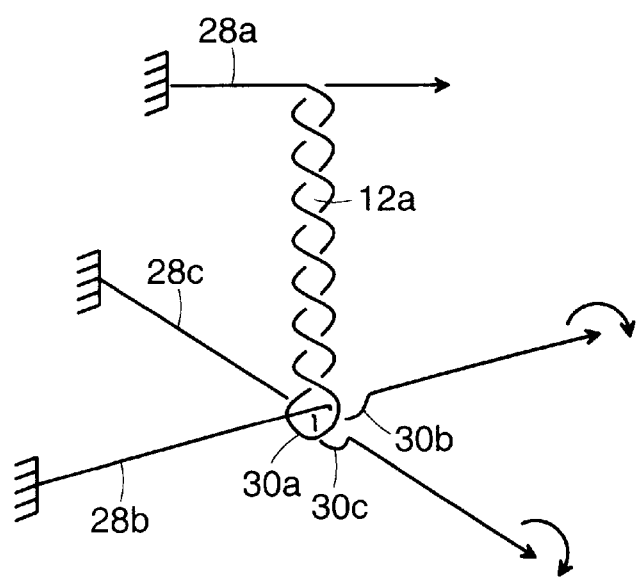

In yet another embodiment, the medical device of the invention can include a medical retrieval basket formed from three wires having three braided legs and an atraumatic basket tip. Referring to FIG. 9G, a basket having these features may be constructed by first making braided leg 12a in the manner described above and illustrated in FIGS. 6A–6E. Next, a crimp 30b, 30c is formed in wire 28b and wire 28c, respectively, in the manner described above and illustrated in FIGS. 6A–6B. Wire 28b is inserted through the loop at the end 30a of leg 12a up to as far as the crimp 30b of wire 28b. Wire 28c is also inserted through the loop at the end 30a of leg 12a up to as far as crimp 30c of wire 28c, respectively. Wires 28b and 28c are twisted as described above and illustrated in FIGS. 6C–6E or 6F to form leg 12b and leg 12c. A basket distal end having a substantially atraumatic tip 40 and three braided legs 12a, 12b, 12c is formed thereby, as illustrated in FIG. 9H. Additional wires may be used to form a basket with more than three braided legs.

Figure 10A:
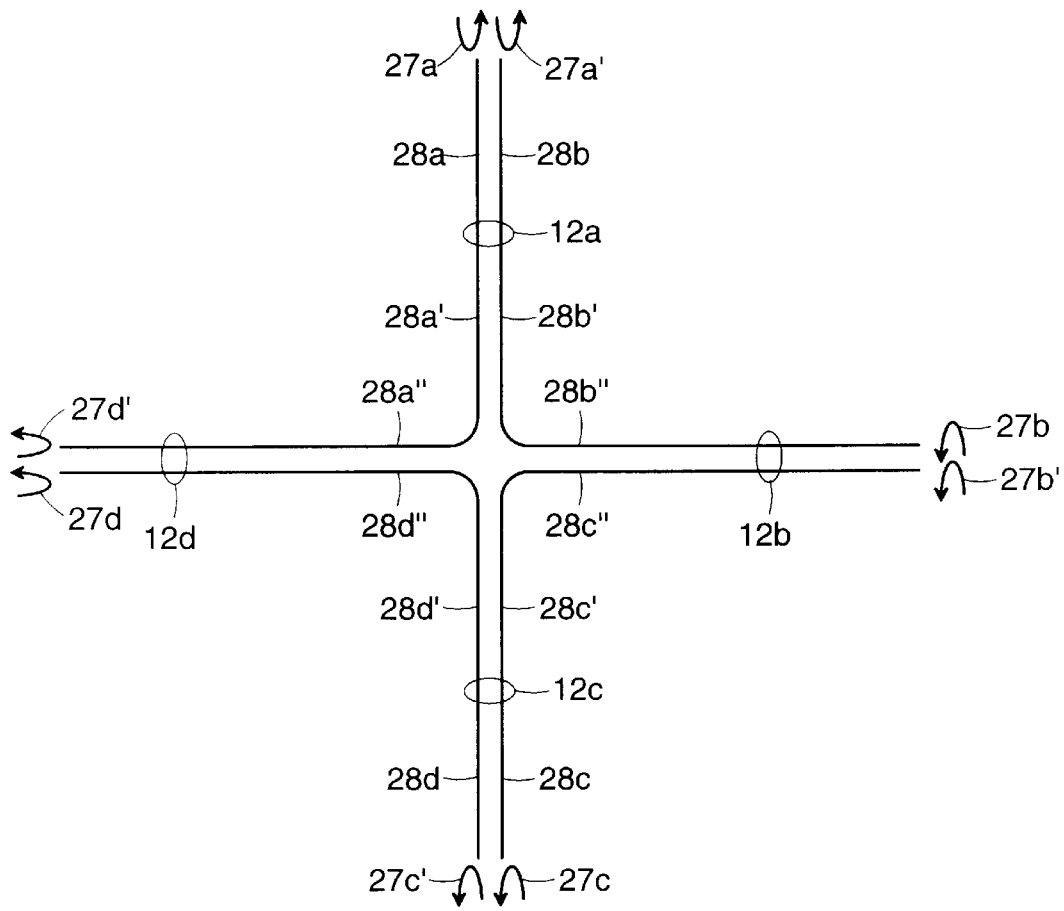
FIGS. 10A–10B show the stages in construction of a four-wire, braided, four-leg basket.
Figure 10B:
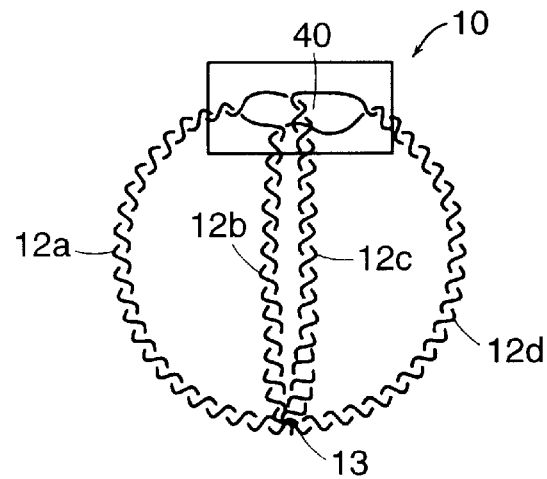
Figure 10C:
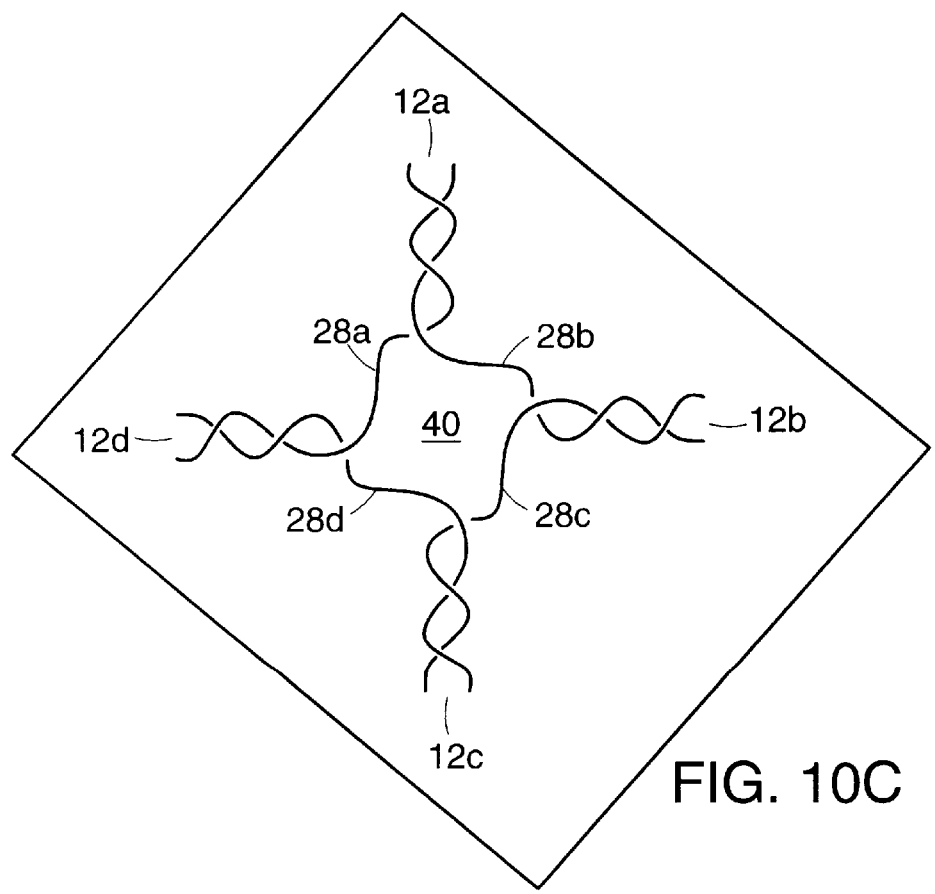
FIG. 10C is an expanded view of the boxed area of the atraumatic basket tip illustrated in FIG. 10B.

In another aspect, the invention relates to a medical device including a medical retrieval basket having four braided legs made from four wires. Referring to FIG. 10A, the first step in a series of steps or stages in construction of four braided legs from four wires is illustrated. In the first step, each of four wires 28a, 28b, 28c, 28d is bent to an angle of about 90° to form two limbs per wire. For example, with continued reference to FIG. 10A, wire 28a is bent to form limb 28a' and 28a", wire 28b is bent to form limb 28b' and 28b", and so on for wires 28c and 28d. Each wire is paired with two other wire limbs to form the shape illustrated in FIG. 10A. For example, wire 28a is paired with wire limb 28b' of wire 28b and wire limb 28d" of wire 28d. Next, parallel pairs of limbs forming the shape illustrated in FIG. 10A are braided together by rotating each of the limbs of a pair simultaneously, and in the direction indicated by arrows 27a and 27a', 27b and 27b', 27c and 27c', 27d and 27d'. For example, wire limb 28a" and 28d" are rotated together to form leg 12d and so on until four braided legs 12a, 12b, 12c, 12d are formed. The ends of braided legs 12a, 12b, 12c, 12d can be brought together to form the base 13 of a medical retrieval basket 10 having an atraumatic tip 40 illustrated in FIG. 10B. The distal tip 40 of the basket 10 is substantially atraumatic as illustrated in FIG. 10C, which is an expanded view of the boxed area of atraumatic tip 40 in FIG. 10B. Baskets having other than four legs made from four wires, such as three legs made from three wires, or five legs made from five wires, are also contemplated by the invention.

Figure 10D:
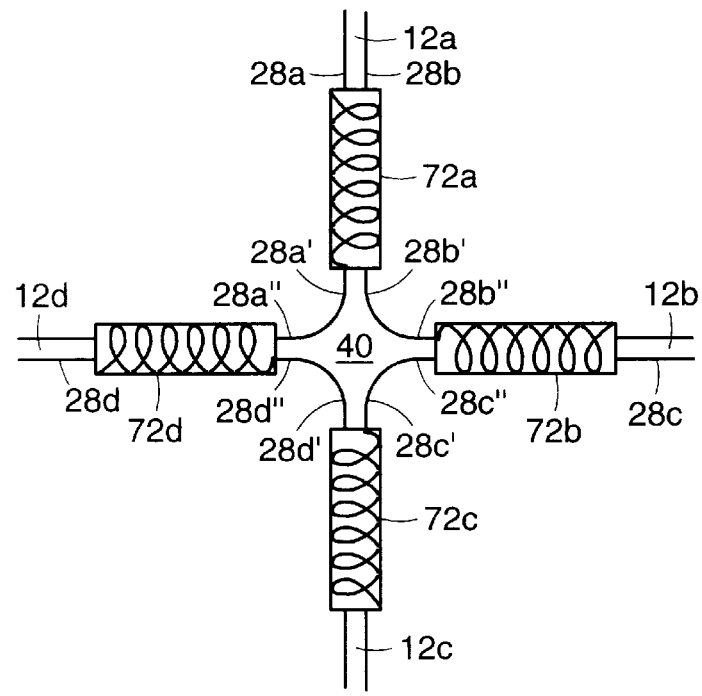
FIG. 10D shows another embodiment of the structure illustrated in FIG. 10A.

In another embodiment of an atraumatic tip of a medical retrieval device, referring to FIG. 10D, the four wires 28a, 28b, 28c, 28d are bent to a 90° angle as described above and illustrated in FIG. 10A. Each bent wire 28a, 28b, 28c, 28d forms two limbs 28a' and 28a", 28b' and 28b", 28c' and 28c", 28d' and 28d", respectively. The limbs are paired as described above and illustrated in FIG. 10A (but not twisted) to form basket legs 12a, 12b, 12c, 12d. Referring to FIG. 10D, a sheath 72a, 72b, 72c, 72d having a lumen (not shown), such as a catheter or coil, encloses each pair of limbs. Each limb, paired with another limb, extends axially within the lumen of one of the sheaths 72*a*, 72*b*, 72*c*, 72*d*. For example, basket leg 12*a* is formed by pairing limb 28*a*' of wire 28*a* and limb 28*b*' of wire 28*b*. Limbs 28*a*' and 28*b*' extend axially within the lumen of sheath 72*a*. Sheath 72*a*, for example, may enclose a portion of leg 12*a* as shown in FIG. 10D, or all of leg 12*a*. The sheath 72*a*, 72*b*, 72*c*, 72*d* is manufactured from flexible material such as, for example, stainless steel, polymers or superelastic alloys, to permit the ends of basket legs 12*a*, 12*b*, 12*c*, 12*d* enclosed by sheaths 72*a*, 72*b*, 72*c*, 72*d*, to be drawn together to form a basket base (not shown). Thus, the distal end of the medical retrieval basket (not shown) formed by the legs illustrated in FIG. 10D is a substantially atraumatic tip 40.

Figure 11A:
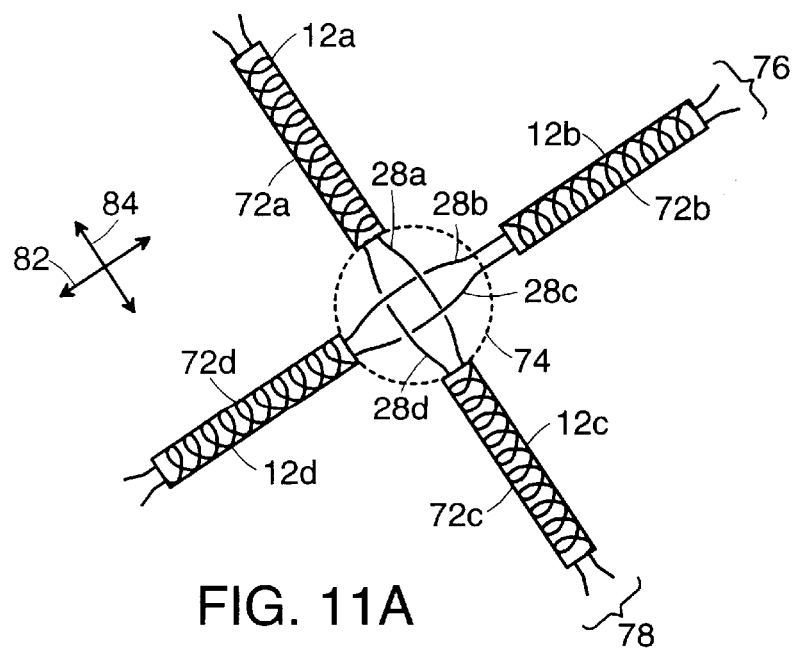
FIG. 11A shows another embodiment of a four wire atraumatic distal tip of a medical retrieval basket having interwoven pairs of wires at the distal tip.

In another aspect, a substantially atraumatic tip of a medical retrieval basket according to the invention, includes four wires that are combined to form two wire pairs 76, 78, each wire pair 76, 78 forming two legs of a medical retrieval basket. As illustrated in FIG. 11A, wires 28*a* and 28*d* are paired to form a first wire pair 78 and wires 28*b* and 28*c* are paired to form a second wire pair 76. Leg pairs 12*a* and 12*c* are formed from wire pairs 78, and leg pairs 12*b* and 12*d* are formed from wire pairs 76. Wires of pair 78 are interwoven with wires of pair 76 at about the mid-section (dashed circle) 74 of each wire where the wire pairs 76, 78 intersect at right angles; pair 76 forming a warp indicated by directional arrow 82 and pair 78 forming a woof indicated by directional arrow 84 to form an atraumatic distal basket tip. In other words, wire 28*a* goes over wire 28*b* and under wire 28*c*. Wire 28*d* goes under wire 28*b* and over wire 28*c*. Wire 28*b* goes over wire 28*d* and under wire 28*a*. Wire 28*c* goes under wire 28*d* and over wire 28*a*. Alternate features of this embodiment of the invention can include a sheath 72*a*, 72*b*, 72*c*, 72*d* such as a coil. Legs 12*a*, 12*b*, 12*c*, 12*d* extend axially within and are enclosed by sheath 72*a*, 72*b*, 72*c*, 72*d*, respectively.

Figure 12A:
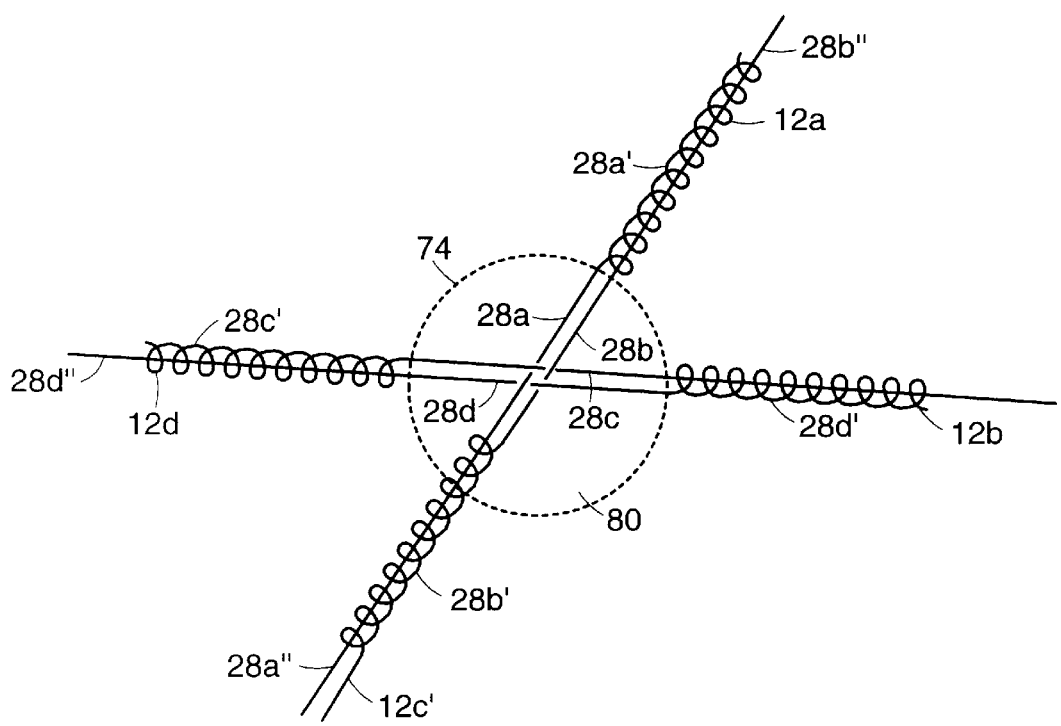
FIG. 12A shows another embodiment of a four wire atraumatic distal tip of a medical retrieval basket having interwoven pairs of wires.

In a variation of the aforementioned embodiment of a substantially atraumatic tip medical retrieval basket described immediately above, illustrated in FIG. 12A, each of the four wires 28*a*, 28*b*, 28*c*, 28*d* of a basket have a coiled end 28*a*', 28*b*', 28*c*', 28*d*' and a straight end 28*a*", 28*b*", 28*c*", 28*d*". As illustrated in FIG. 12A, each of the four legs 12*a*, 12*b*, 12*c*, 12*d* include a straight end 28*a*", 28*b*", 28*c*", 28*d*" and a coiled end 28*a*', 28*b*', 28*c*', 28*d*'. The straight end of one wire in a pair extends axially within the coils of another wire forming the pair of wires of a leg as shown in FIG. 12A. For example, leg 12*a* is formed by pairing coiled end 28*a*' of wire 28*a*, and straight end 28*b*" of wire 28*b*; leg 12*b* is formed by pairing coiled end 28*d*' of wire 28*d*, and straight end 28*c*" of wire 28*c*, and so on for the remaining two legs 12*c*, 12*d*. The four wires 28*a*, 28*b*, 28*c*, 28*d* are interwoven at about the mid-section of each wire (outlined by dashed circle) 74 where, each pair of wires intersects the other pair at about 90°.

Figure 13A:
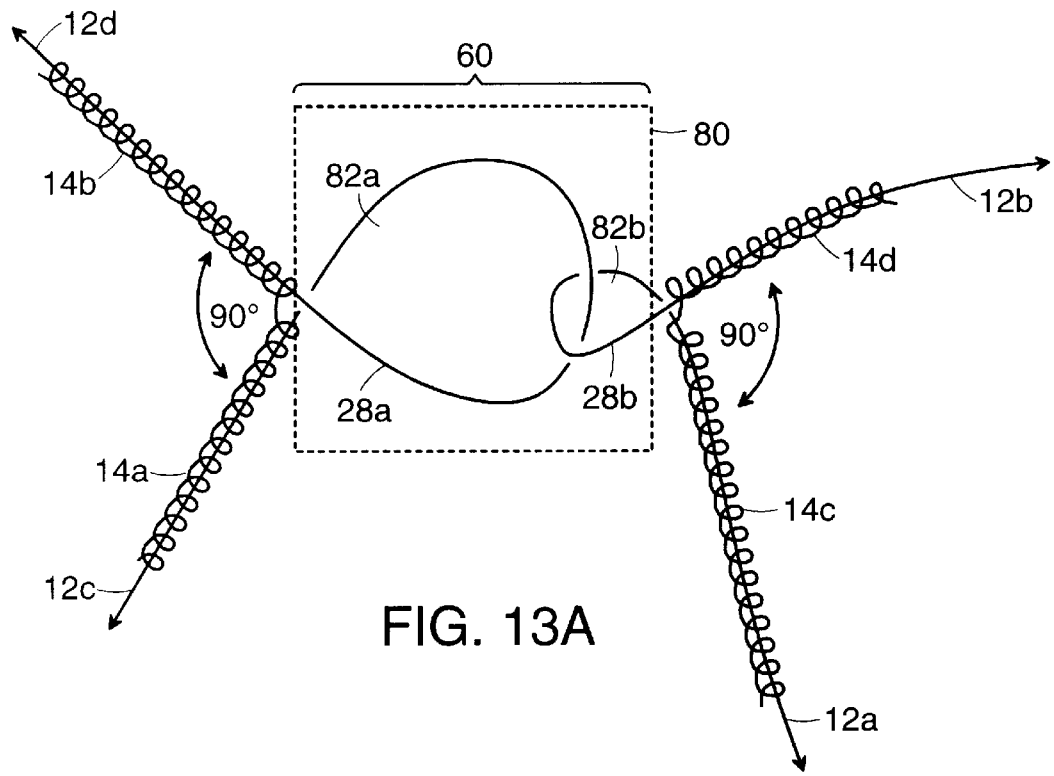
FIG. 13A shows a stage in the construction of another embodiment of a two wire atraumatic distal tip of a medical retrieval basket.
Figure 13B:
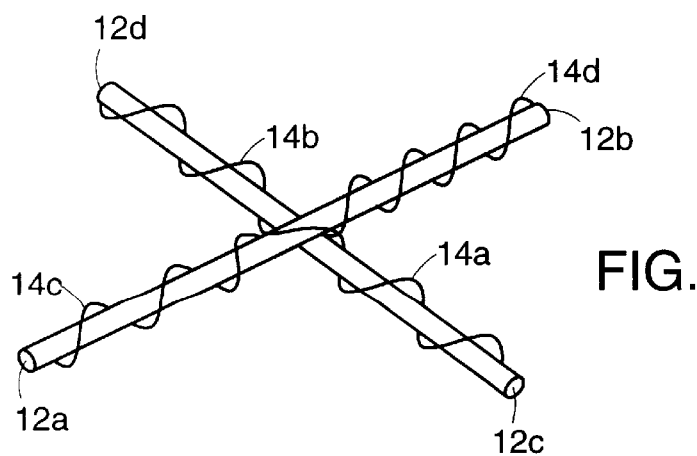
FIG. 13B shows an embodiment of an atraumatic distal tip formed according to the method illustrated in FIG. 13A.

In another aspect, the invention relates to a medical device having a distal end portion and two wires forming four legs that extend proximally from the distal end portion to form a medical retrieval basket. Referring to FIG. 13A, a distal end portion 60 is illustrated with four legs 12*a*, 12*b*, 12*c*, 12*d* formed by two wires 28*a*, 28*b*. Leg pairs 12*a* and 12*b* are formed by wire 28*b* and leg pairs 12*c*, 12*d* are formed by wire 28*a*. At about the mid-section (boxed area) 80 of wire 28*a*, loop 82*a* is formed and at about the mid-section (boxed area) 80 of wire 28*b*, loop 82*b* is formed. Wire loop 82*a* is linked through wire loop 82*b* as shown in FIG. 13A. The two ends of wire 28*a* extend from loop 82*a* to form legs 12*c*, 12*d*. A coil made from a single length of wire forms a sheath enclosing a pair of legs formed by a single basket wire. For example, as illustrated in FIG. 13A, leg 12*a* formed from a single wire 28*b* is enclosed by sheath 14*c* and leg 12*b* formed from single wire 28*b* is enclosed by sheath 14*d*. Sheath 14*c* and 14*d* are formed from a common wire. Legs 12*a*, 12*b*, 12*c* and 12*d* are pulled in the direction indicated by the arrows at the end of each leg to cause wires 28*a* and 28*b* to straighten. Thus, in this embodiment of an atraumatic tip of a medical retrieval basket according to the invention, the distal basket end 60 is formed by linking together wire loop 82*a* and 82*b*, followed by straightening wires 28*a* and 28*b* to remove loops 82*a* and 82*b* to form an atraumatic tip as illustrated in FIG. 13B. Each leg 12*a*, 12*b*, 12*c*, 12*d* of the basket is ensheathed by a coil 14*a*, 14*b*, 14*c*, 12*d*.

All of the above-described embodiments have in common, a substantially atraumatic basket tip according to the invention.

In yet another aspect, the invention relates to a method for retrieving material from a body such as a body tract or body canal. Material (e.g., biological or foreign) can be retrieved from a body by using a basket with an atraumatic tip where the atraumatic tip is formed by entwining the legs of the basket at the basket tip or by coupling braided legs of the basket at the basket tip. The basket of the retrieval device has an atraumatic distal end and thus allows the capture of material that is located in pockets or other difficult-to-access areas within the body. Because the distal basket end is atraumatic, it can make intimate contact with the surface of tissue, even the walls or lining of a pocket-type area, and allow the retrieval of stones or other materials that are unrecoverable with conventional tipped baskets that can cause tissue trauma and are limited in how close the basket can get to the tissue by the existence of the protruding tip.

A method for retrieving material from a body includes inserting a retrieval device according to the invention into the body, moving the tipless basket into the extended position, maneuvering the basket via the proximal handle (which is located outside of the body) of the retrieval device until the material (e.g., stone) is entrapped within the three-dimensional basket structure, and then capturing the material within the basket by moving the basket relative to the sheath to close the basket legs around the material. With the material so gripped or held by the basket, the basket can be withdrawn from the body to remove the material from the body. Before the basket is withdrawn from the body with the captured material, the material can be broken apart by, for example, laser energy or lithotripsy. Mechanisms for breaking up the material before its removal from the body can be part of the retrieval device or can be separate tools/devices that are also inserted into the body and utilized at the appropriate time in the stone removal procedure. The material that can be captured with tipless baskets according to the invention includes a calculus, or a stone, such as a kidney stone, a ureteral stone, a urinary bladder stone, a gall bladder stone, or a stone within the biliary tree.

Variations, modifications, and other implementations of what is described herein will occur to those of ordinary skill in the art without departing from the spirit and the scope of the invention as claimed. Accordingly, the invention is to be defined not by the preceding illustrative description but instead by the spirit and scope of the following claims.

What is claimed is:

1. A medical device, comprising:
 a plurality of legs forming a basket for retrieving material from a body; and
 a tip at a distal end of the basket, said tip comprising two or more of the legs knotted and tightened together.

2. The medical device of claim 1 further comprising an elongated member, said elongated member and one of said legs comprising a single wire.

3. The medical device of claim 1 wherein said two or more knotted legs include a distal segment said distal segment forming at least one other of the legs of the basket.

4. The medical device of claim 3 further comprising an elongated member wherein a portion of said distal segment is attached to said elongated member.

5. The medical device of claim 1 wherein each of the legs is braided and the legs are each formed from a single wire.

6. The medical device of claim 1 wherein said knot comprises a square knot or a granny knot.

7. The medical device of claim 6 wherein said basket comprises two wires, each of said wires having a knot, and each of said knots knotted together at the distal end of said basket.

8. The medical device of claim 1 wherein said tip at said distal end of said basket comprises a plurality of knots.

9. A medical device, comprising:
a basket for retrieving material from a body, the basket comprising a distal end and a plurality of legs extending proximally from the distal end, both the distal end and the plurality of legs being formed integrally from a single twisted wire.

10. The medical device of claim 9 wherein said legs comprise at least one braided leg.

11. The medical device of claim 9 wherein at least a portion of one of the legs is braided.

12. The medical device of claim 9 wherein the legs are formed from at least one twisted wire and are twisted together at said distal basket end portion.

13. The medical device of claim 9 wherein said plurality of legs are formed from a plurality of twisted wires.

14. The medical device of claim 9 wherein said distal end portion of the basket comprises a knot.

15. The medical device of claim 14 wherein said knot comprises two wire loops twisted together.

16. The medical device of claim 15 wherein said knot comprises a square knot or a granny knot.

17. The medical device of claim 9 wherein said distal end of the basket comprises a plurality of loops, said loops being twisted together at said distal end of the basket.

18. A medical device, comprising:
a basket comprising a distal end and a plurality of pairs of twisted basket legs extending proximally from the distal end, each of the pairs of basket legs being formed from a single twisted wire, the distal end being formed by entwining together the pairs of basket legs.

* * * * *

UNITED STATES PATENT AND TRADEMARK OFFICE
CERTIFICATE OF CORRECTION

PATENT NO. : 6,159,220  
DATED : December 12, 2000  
INVENTOR(S) : Gobron et al.

Page 1 of 1

It is certified that error appears in the above-identified patent and that said Letters Patent is hereby corrected as shown below:

<u>Title page</u>
Under "U.S. Patent Documents":
-- 5,989,266   11/1999   Foster   606/127
   5,484,384             Fearnot  600/3
   5,496,330             Bates    600/127
   4,046,150   9/1997    Schwartz --
Under "Foreign Patent Documents":
-- DE 19703482   DE
   EP 0765636    EP
   WO 99/0867    WIPO --
Under "Foreign Patent Documents":
-- Other Publications
Copy of International Search Report for PCT/US00/05996 marked July 18, 2000
Copy of Precis of DE 19703482 --

Signed and Sealed this

Ninth Day of October, 2001

*Attest:*

NICHOLAS P. GODICI
*Attesting Officer*   Acting Director of the United States Patent and Trademark Office